United States Patent [19]

Katsuyama et al.

[11] Patent Number: 4,902,477
[45] Date of Patent: Feb. 20, 1990

[54] ANNALYTICAL ELEMENT FOR QUANTITATIVE ANALYSIS OF BILIRUBIN

[75] Inventors: Harumi Katsuyama; Shigeki Kageyama, both of Saitama; Kumiko Sato, Kanagawa, all of Japan

[73] Assignee: Fuji Photo Film Co., Ltd., Kanagawa, Japan

[21] Appl. No.: 273,631

[22] Filed: Nov. 17, 1988

Related U.S. Application Data

[63] Continuation of Ser. No. 578,284, Feb. 8, 1984, abandoned.

[30] Foreign Application Priority Data

Feb. 9, 1983 [JP] Japan .................................. 58-21171

[51] Int. Cl.[4] ...................... G01N 21/78; G01N 33/72
[52] U.S. Cl. ......................................... 422/56; 420/57; 436/97; 436/170; 436/903
[58] Field of Search ............... 422/56, 57, 58; 436/97, 436/169, 170, 903

[56] References Cited

U.S. PATENT DOCUMENTS

| | | | |
|---|---|---|---|
| 3,992,158 | 11/1976 | Przybylowicz et al. | 422/58 X |
| 4,069,017 | 1/1978 | Wu et al. | 436/97 |
| 4,258,001 | 3/1981 | Pierce et al. | 422/56 |
| 4,468,467 | 8/1984 | Babb et al. | 436/97 |
| 4,557,901 | 12/1985 | Koyame et al. | 422/56 |
| 4,562,148 | 12/1985 | Sommer | 422/56 X |
| 4,576,793 | 3/1986 | Koyama et al. | 422/56 |
| 4,604,347 | 8/1986 | Arai et al. | 422/56 X |
| 4,671,937 | 6/1987 | Katsuyama et al. | 422/56 |

*Primary Examiner*—Robert J. Hill, Jr.
*Attorney, Agent, or Firm*—Jules E. Goldberg

[57] ABSTRACT

An analytical element for quantitative analysis of bilirubin in a liquid sample by a diazo method, characterized in that the bilirubin detection reagent is a non-diffusive aryldiazonium salt having in the aryl group at least one substituent selected from the group consisting of an alkoxycarbonyl group, an alkylaminosulfonyl group and an alkylaminocarbonyl group.

4 Claims, 2 Drawing Sheets

FIG.I

ANNALYTICAL ELEMENT FOR QUANTITATIVE ANALYSIS OF BILIRUBIN

This is a continuation of application Ser. No. 578,284, filed Feb. 8, 1984, now abandoned.

BACKGROUND OF THE INVENTION

1. Field of the Invention

The present invention relates to an analytical element for quantitative analysis of bilirubin, and more particularly to an analytical element employable for quantitative analysis of bilirubin based on a dry process operation with high accuracy by a simple and quick operation.

2. Description of Prior Arts

Bilirubin, a principal component of a bile pigment in a body fluid, is produced in serum by decomposition of heme originating from hemoglobin in red blood corpuscle. Bilirubin is then absorbed by a liver, in which bilirubin is converted to a glucuronic acid-conjugated product, etc. and excreted in bile. The content of bilirubin in blood increases in response to increase of decomposition of hemoglobin as well as decrease of the liver function. Accordingly, the quantitative analysis of bilirubin is considered to be an indispensible test item in the clinical test.

As the method for quantitative analysis of bilirubin in serum, there are known a quantitative analysis method comprising photometric measurement of the yellow color inherently attached to the bilirubin, and a colorimetric analysis of red azobilirubin produced by coupling reaction of bilirubin and diazotized sulfanilate (p-sulfobenzenediazonium salt, Ehrlich reagent) based on Ehrlich reaction discovered by Van den Bergh. The latter method is named a diazo method.

Details of methods for quantitative analysis of bilirubin in serum are described in "Comprehensive Text of Clinical Test Technology" edited by Ishii, Vol. 6, pp. 332–350 (Igaku Shoin, 1975).

Details of the diazo method are further described below.

Bilirubin produced in serum by the decomposition of heme is named free bilirubin. This bilirubin is as such hydrophobic, but is dissolved in serum in combination with serum albumin, being adsorbed by the serum alubmin. The free bilirubin introduced into liver is combined with glucuronic acid through covalent bond to become conjugated with glucuronic acid. Thus, a glucuronic acid-conjugated bilirubin which is enhanced in the water-solubilitiy by the aid of the hydrophilic group contained in the glucuronic acid is produced. Also known is a highly water-soluble bilirubin combined to serum albumin, but no production mechanism is known on this produce (J. J. Lauff, et al., Clinical Chemistry, 28(4), 629–637 (1982)).

Among these various bilirubins, the highly watersoluble conjugated bilirubin and the albumin-conjugate bilirubin both easily react with a diazonium salt, and are directly subjected to colorimetry. Accordingly, these bilirubins are named direct bilirubins.

The hydrophobic free bilirubin undergoes coupling reaction in the presence of a reaction accelerator such as caffeine, sodium benzoate, sodium acetate, dyphylline (C. A. Registory No. [479-18-5]), urea, a nonionic surfactant, gum arabic, an alcohol (e.g., methanol, ethanol), an acid amide, sulfoxide, etc., to produce axobilirubin. Therefore, the quantitative analysis of free bilirubin is generally performed indirectly by a stage of colorimetrically determining the total bilirubin content in a liquid sample in the presence of a reaction accelerator and a subsequent stage of subtracting the direct bilirubin content determined separately in the absence of a reaction accelerator from the total bilirubin content. For this reason, the free bilirubin is otherwise named an indirect bilirubin.

Details of the diazo method for quantitative analysis of bilirubin are described in the following publications: M. Michaelsson, Scand. J. Clin. Lab. Invest., 13 (Suppl.), 1–80 (1961); H. Malloy, J. Biol, Chem., 119, 481(1939); and Z. K. Shihabi, et al., American Journal of Medical Technology, 43(10), 1004–1007(1977).

As for the diazonium salt employed in the bilirubin analysis based on the diazo method, improvements have been recently made with respect to the detection sensitivity and stability of the produced azobilirubin. For instance, halobenzenediazonium salts such as 2,4-dichlorophenyldiazonium salt and 2-chloro-4-nitrophenyldiazonium, and stabilized diazonium salts (stabilized by the use of counter ions) developed by Kulhanek, Erthinghansen, et al. are generally utilized. The history of such development is understood, for instance, by referring to Japanese Patent Publication No. 54(1979)-12840, and Japanese Patent Provisional Publications Nos. 55(1980)-4492, 56(1981)-10255, 56(1981)-12555 and 57(1982)-103056.

As described above, a colorimetric analysis method comprising performing a color reaction in proportion to the content of an analyte (substance to be analyzed) and subsequetnly measuring the color formation to determine the content of the analyte is well known. This method is utilized not only in a wet analysis process but also in a dry analysis process.

The dry process (i.e., dry analysis process) is based on a colorimetric analysis utilizing a dry analytical element in the form similar to the pH test strip, which comprises a paper sheet or absorbent carrier impregnated with a reagent to produce a color in contact with an analyte.

As the dry analytical element, there is known a multilayer analytical element capable of giving highly precise analytical result. For instance, multilayer analytical element described in Japanese Patent Publication No. 53(1978)-21677 (corresponding to U.S. Pat. No. 3,992,158), and Japanese Patent Provisional Publications Nos. 50(1975)-137192 (U.S. Pat. No. 3,983,005), 51(1976)-40191 (U.S. Pat. No. 4,042,335), 52(1977)-3488 (U.S. Pat. No. Re. 30,267), 53(1978)-89796 (U.S. Pat. No. 4,069,017), 53(1978)-131089 (U.S. Pat. No. 4,144,306), etc. are in the form of a laminated structure comprising a support, one or more reagent layers on the support, and a porous, nonfibrous spreading layer on the reagent layer.

The above-mentioned multilayer analytical element is constructed in such a manner that a liquid sample applied (for instance, spotted) on the spreding layer permeates into the reagent layer, keeping a substantially constant amount per a unit area, and shows therein a color reaction. Accordingly, the content of the analyte in the liquid sample can be determined by measuring the color density after the lapse of a certain period of time.

A multilayer analytical element for quantitative analysis of bilirubin based on the dry process is already known. This element utilized a color reaction between bilirubin and diazotized sulfanilate (p-sulfobenzenediazonium, a bilirubin detection reagent) in the reagent layer thereof.

However, since the above-mentioned diazonium salt is highly hydrophilic and of high polarity, some problems are brought about into the analytical process employing the multilayer analytical element. For example, in the course of diffusion of the liquid sample into the reagent layer after spotting the liquid sample on the spreading layer of the analytical element, the diazonium salt is liable to be distributed ununiformly through the so-called chromatographic behavior to reduce the uniformal distribution of the azobilirubin showing color.

Moreover, the diazonium salt is liable to diffuse between the layers in the course of the preparation and storage of the multilayer analytical element, whereby the accuracy of the bilirubin analysis decreases as the time progresses. This means that the effectively employable period of the analytical element is shortened.

Into the multilayer analytical element, certain improvements have been introduced for enhancing the accuracy of the measurement. For instance, a light-blocking layer and an isotropically porous spreading layer are provided to the element. Otherwise, the diazonium salt is locally located in the analytical element. Even in thus improved multilayer analytical elements, the above-mentioned low molecular weight diazonium salt contained in the reagent layer is very liable to diffuse into the light-blocking layer and spreading layer, in the course of the preparation and storage thereof. The high diffusive prorperty of this diazonium salt is considered to arise from its low molecular weight. In the multilayer analytical element containing thus diffused diazonium salt, bilirubin contained in a liquid sample spotted thereon produced a not a small amount of azobilirubin even within the light-blocking layer and spreading layer. Accordingly, the total bilirubin produced by bilirubin and the diazonium salt cannot be quantitatively measured by a refelection optical measurement. In other words, the measured value shows negative error.

SUMMARY OF THE INVENTION

A primary object of the present invention is to provide an analytical element employable for quantitatively analyzing bilirubin in a liquid sample, simply, quickly and very accurately.

Another object of the invention is to provide an analytical element containing a nondiffusive diazonium salt for quantitative analysis of bilirubin which is so improved that the diffusion of diazonium salt occurring in the course of the preparation and storage of the element is effectively prevented, whereby the error in measurement is remarkably reduced.

The present invention provides an analytical element for quantitative analysis of bilirubin in a liquid sample by a diazo method, characterized in that a bilirubin detection reagent is a nondiffusive aryldiazonium salt having in the aryl group at least one substituent selected from the group consisting of an alkoxycarbonyl group, an alkylaminosulfonyl group and an alkylaminocarbonyl group.

DETAILED DESCRIPTION OF THE INVENTION

Figure 1:
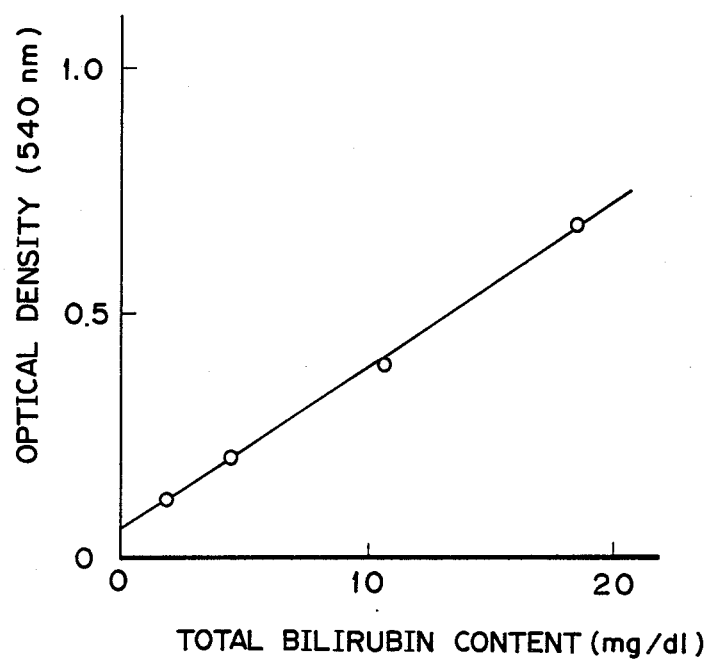
FIG. 1 shows graphically a relationship between the total bilirubin content and the optical density of the color, obtained in the analysis of bilirubin described in Example 1.

A representative embodiment of the analytical element of the present invention is in the form of a multilayer analytical element comprising a liquid sample-spreading layer (or simply spreading layer), one or more reagent layers, and a liquid-impermeable, light-transmissive support.

In the above-mentioned constitution, the support and liquid sample-spreading layer are known in their materials and constitutions. Accordingly, the support and liquid sample-spreading layer employable for constituting the multilayer analytical element according to the invention can be optionally formed utilizing these known materials and constitutions. If desired, one or more of functional layers known in the structures of the conventional multilayer analytical elements, for instance, a light-reflecting layer, a light-blocking layer, a diffusion-preventing layer, and an adhesive layer (to be attached to the reagent layer) can be provided in the element.

If the laminated structure comprising the reagent layer and liquid sample-spreading layer is in the form of a self-supporting integrated sheet, the reagent layer and/or the liquid sample-spreading layer as such can serve as a support replacing the independent support. The liquid sample-spreading layer is not essential to the constitution of the analytical element of the present invention.

The analytical element of the present invention contains, as a bilirubin detection reagent, a nondiffusive (diffusion-resistant) aryldiazonium salt having a specific substitutent or substituents.

The aryldiazonium salt utilizable in the present invention contains in the aryl group (preferably a benzene ring) at least one substituent selected from the group consisting of an alkoxycarbonyl group, an alkylaminosulfonyl group and an alkylaminocarbonyl group (in which each of the alkyl and alkoxy preferably contains 2–22 carbon atoms), and preferably further contains at least one substituent selected from the group consisting of an alkyl group and an alkoxy group (in which each of alkyl and alkoxy preferably contains 1–12 carbon atoms).

Representative examples of the aryldiazonium salt utilizable in the present invention are given below, but these examples are by no means construed to restrict the invention:

1: 2-methoxy-5-(tetradecyloxycarbonyl)benzenediazonium tetrafluoroborate,
2: 2-methoxy-5-(tetradecyloxycarbonyl-benzenediazonium hexafluoroborate,
3: 2-ethoxy-5-(hexadecyloxycarbonyl)benzenediazonium tetrafluoroborate,
4: 2-dodecyloxy-5-(ethoxycarbonyl)benzenediazonium tetrafluoroborate,
5: 2- thoxy-5-[β-(2',4'-di-t-amylphenoxy)ethoxycarbonyl]benzenediazonium tetrafluoroborate,
6: 2-methoxy-5-(N-hexadecylsulfamoyl)benzenediazonium tetrafluoroborate,
7: 2-propoxy-5-(N-tetradecylsulfamoyl)benzenediazonium perchlorate,
8: 2-octyloxy-5-(N-decylsulfamoyl)benzenediazonium hexafluorophosphate, 9: 3,5-bis(dodecyloxycarbonyl)benzenediazonium tetrafluoroborate, 10: 3,5-bis(tetradecyloxycarbonyl)benzenediazonium tetrafluoroborate, 11: 2-methoxy-5-(N-tetradecylcarbomoyl)benzenediazonium tosylate, 12: 2-methoxy-5-[N-(4-t-amylphenoxyethyl)carbamoyl]benzenediazonium 1-naphthalenesulfonate, 13: 4-(hexadecyloxycarbonyl)benzenediazonium tetrafluoroborate 14: 4-(N-hexadecylsulfamoyl)benzenediazonium tetrafluoroborate, 15: 3-hexadecylcarbonylbenzenediazonium tetrafluoroborate, 16: 3-(N-tetradecylcarbamoyl)benzenediazonium tetrafluoroborate, 17: 2-methyl-5-tetradecyloxycarbonylbenzenediazonium tetrafluoroborate, 18: 2-butyl-5-decyloxycarbonylbenzenediazonium tetrafluoroborate, 19: 4-{N-[γ-(2',4'-di-t-amylphenoxy)propyl]carbamoyl} benzenediazonium tetrafluoroborate, and 20: 4-[β-(2',4'-di-t-amylphenoxy)ethoxy]carbonylbenzenediazonium tetrafluoroborate.

The aryldiazonium salt such as above is generally contained in the reagent layer of the analytical element.

There is no specific limitation on the material of constitution of the reagent layer employable in the analytical element of the invention, and a known art is applicable to the prepareation of a reagent layer containing an aryldiazonium salt.

However, the reagent layer of the element preferably is in the form of a porous reagent layer so that the diffusion of bilirubin (analyte) can be easily accomplished. The porous reagent layer preferably is in the form of a porous matrix comprising solid fine particles and a binder.

The above-mentioned porous matrix comprising solid fine particles and a binder is formed by porous fine particles or nonporous fine particles such as microcrystalline cellulose, cellulose micropowder, silicate fine particles such as silica, diatomaceous earth, or polymer microbeads, and a binder combining these fine particles to form a porous structure having continuous voids.

As the binder employable for the formation of the porous matrix, a hydrophilic polymer or polymer latex particles containing at least 2% of a hydrophilic repeating unit. Examples of the hydrophilic polymer include homopolymers containing a repeating unit derived from styrene - p-sulfonic acid, acrylic acid, methacrylic acid, a maleic acid derivative, acrylamide, methacrylamide, N-(sulfoalkyl)acrylamide, N-(sulfoalkyl)methacrylamide, N-alkylacrylamide, N-alkylmethacrylamide, N-(hydroxyalkylacrylamide, N-vinylpyrroidone, N-vinylimidazole, vinyl alcohol, hydroxyethyl methacrylate, hydroxyethylacrylamide and the like, as well as copolymers containing two or more repeating units derived from the above-mentioned repeating units. Copolymers containing the repeating unit derived from the above-mentioned monomer as well as one or more repeating units derived from other monomers can be also employed. Preferably, the binder is an acidic polymer.

The reactivity between bilirubin and a diazonium salt is prominently influenced by the solubility of the bilirubin. Since the free bilirubin (indirect bilirubin) of nonconjugate type is highly hydrophobic and poorly water soluble, the rate of reaction with a diazonium is low. In contrast, since the conjugate bilirubin and albumin-conjugated bilirubin are highly soluble in water, these rapidly reacts with a diazonium salt. Accordingly, the difference on the reaction rate residing between a variety of bilirubins is utilized to analyze separately each of the direct bilirubin (conjugate or protein-conjugated bilirubin) and the indirect bilirubin (free bilirubin).

The analytical element of the present invention can be employed in the same manner to separately analyze each of the direct and indirect bilirubins.

In the quantitative analysis of the total bilirubin content or a quick analysis of the indirect bilirubin, a reaction accelerator is necessarily included in the analytical element. The reaction accelerator employable for this purpose is known and described in a variety of texts. Examples of the accelerator include alcohols (e.g., methanol, ethanol, etc.), caffeine, sodium benzoate, sodium acetate, dyphylline (C. A. Registry No. [479-18-5]), urea, a nonionic surfactant, gum arabic, an acid amide, sulfoxide, etc. The reaction accelerator can be optionally incorporated into the analytical element of the present invention.

The present invention is further described by the following examples.

EXAMPLE 1

The aryldiazonium salt defined in the present invention was evaluated in the form of a solution containing it with respect to the function as a bilirubin detection reagent.

| Formulation of aryldiazonium salt solution | |
| --- | --- |
| 2-Methoxy-5-(tetradecyloxycarbonyl)benzenediazonium tetrafluoroborate | 500 mg. |
| Acetone | 15 ml. |
| Ethanol | 40 ml. |

200 μl. of this aryldiazonium salt solution was added to 100 μl. of each of various control serums in 2 ml. of 10% aqueous acetic acid, and the reaction was carried out in the mixture at 25° C. for 1 min. Subsequently, the reaction mixture was taken up into a cuvette (lightpath: 10 mm) and the optical density thereof was measured photometrically at a wavelength of 540 nm to determine the content of the produced azobilirubin.

Independently, the total bilirubin content was determined by the use of ABA-200 (available from Abbott Laboratories).

The results are set forth in Table 1.

TABLE 1

| | Total Bilirubin Content (mg/dl) | Optical Density (540 nm) |
| --- | --- | --- |
| Human albumin solution | 0 | 0.065 |
| Monitrol I (Dade Corp.) | 1.8 | 0.117 |
| Monitrol II (Dade Corp.) | 4.3 | 0.204 |
| Hepatest (Daiichi Seiyaku Co., Ltd., Japan) | 10.6 | 0.395 |
| Versatol P (General Diagnostic Corp.) | 18.6 | 0.683 |

The relationship between the bilirubin content and the optical density is graphically illustrated in FIG. 1. FIG. 1 clearly indicates linear relationship between the bilirubin content and the optical density at 540 nm.

COMPARISON EXAMPLE 1

To each 200 ml. of the diazonium salt (diazotized sulfanilate) solution attached to a commercially available bilirubin analysis kit and the aryldiazonium salt solution of Example 1 was added each 100 μl. of a control serum in 2 ml. of 10% aqueous acetic acid. The color reaction was carried out in the mixture at 25° C. for 1 min. Subsequently, the reaction mixture was taken up into a cuvette (lightpath: 10 mm) and the absorption sepctrum was taken. The absorption spectra given in the use of the diazotized sulfanilate and the aryldiazonium salt are shown in FIG. 2.

Figure 2:
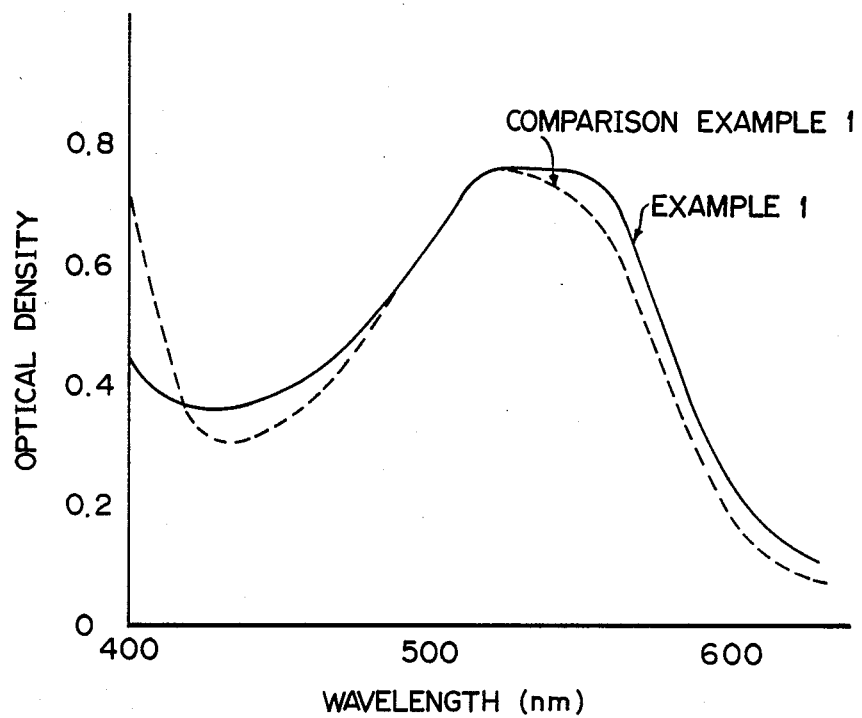
FIG. 2 shows absorption spectra of azobilirubins produced in the use of a compound belonging to the aryldiazonium salt defined in the present invention as well as in the use of the conventional diazotized sulfanilate (p-sulfobenzenediazonium salt).

The absorption spectra shown in FIG. 2 indicate that the aryldiazonium salt (Example 1) gives an optical density at a level substantially similar to that of the diazotized sulfanilate (standard reference compound employed in a bilirubin analysis according to the conventional diazo method). Accordingly, it is understood that the aryldiazonium salt has a satisfactory bilirubin detection ability. The absorption spectra further indicate that the spectrum of an azobilirubin produced in the use of the standard reference compound has the absorption maximum at 520 nm, while the spectrum of an azobilirubin produced in the use of the aryldiazonium salt of Example 1 has the absorption maximum in a wide range of 520 to 550 nm in a longer wavelength region. Accordingly, it is concluded that the aryldiazonium salt of Example 1 is advantageously employed in the analysis of bilirubin.

EXAMPLE 2

To 10 g. of 5% aqueous solution of methyl vinyl ether - maleic anhydride (1:1, molar ration) copolymer (GANTRETZ AN-139, tradename of GAF Corp., inherent viscosity [η] at 25° C. in 1% methyl ethyl ketone solution: 1.0–1.4) was added 5 ml of the aryldiazonium salt solution described in Example 1 (according to the present invention). To the resulting mixture was added 100 ml. of water to prepare a solution for impregnation.

Each of a cellulose acetate membrane filter (mean pore size 0.3 μm, thickness 140 μm) and a paper filter (thickness 100 μm) was impregnated with the above-mentioned solution at approx. 100 g/m², and then allowed to stand on a hydrophilically processed plastic support to dryness. Thus, multilayer analytical elements for quantitative analysis of bilirubin were prepared.

10 μl. of a commercially available high bilirubin content control serum (Versatol P or Omega (high bilirubin content)) was spotted at room temperature on each of the multilayer analytical elements. At 3 min. after the spotting, the optical density of color formed on the element was measured by reflection photometry through a green filter. The results are set forth in Table 2.

TABLE 2

| | Optical Density | |
|---|---|---|
| | Membrane filter | Paper filter |
| Versatol P | 0.51 | 0.49 |
| Omega (high bilirubin content) | 0.52 | 0.50 |

To 10 g. of 5% aqueous solution of methyl vinyl ether - maleic anhydride (1:1, molar ration) copolymer (GANTRETZ AN-139, tradename of GAF Corp., inherent viscosity [η] at 25° C. in 1% methyl ethyl ketone solution: 1.0 - 1.4) was added 5 ml of the aryldiazonium salt solution described in Example 1. To the resulting mixture were added 10 ml. of water and 5 g. of microcrystalline cellulose (Avicel, trademark) to prepare a coating solution.

The coating solution was coated over a transparent polyethylene terephthalate support to form a layer of 20 μm thick (thickness upon dryness). On this layer was coated 1% aqueous solution of methyl vinyl ether - maleic anhydride (1:1, molar ratio) copolymer, and immediately after the coating was complete, Fuji Microfilter FM 120 (trademark of Fuji Photo Film Co., Ltd., Japan, membrane filter made of cellulose acetate-type blushed polymer, mean pore size 1.2 μm, thickness 180 μm) having been dried after processing with 0.2% aqueous p-nonylphenoxypolytglicidol, was pressed onto the coated copolymer solution. Thus, an integrated analytical element was prepared.

A pure free bilirubin was dissolved in 5% aqueous human albumin solution containing sodium carbonate to prepare indirect bilirubin solutions of three different content levels.

Each bilirubin soltuion was spotted on the analytical element, and at 4 min, after the spotting, the optical density of color formed on the element was measured by reflection photometry through a green filter. The results are set forth in Table 3.

TABLE 3

| Indirect Bilirubin Content (mg/dl) | ΔOD |
|---|---|
| 5 | 0.23 |
| 10 | 0.32 |
| 20 | 0.50 |

Remark: "ΔOD" means a value obtained by subtracting

Remark: "ΔOD" means a value obtained by subtracting from the measured value a value obtained by measurement performed in the same manner except for employing simple 5% aqueous human albumin solution.

EXAMPLE 4

On a transparent polyethylene terephthalate support was coated 10% aqueous deionized-gelatin solution to form an absorbent layer of 10 μm thick (thickness upon dryness).

Separately, various coating soltuions were prepared under the following formulation using various aryldiazonium salts:

| | |
|---|---|
| Aryldiazonium salt | 40 mg. |
| Diatomaceous earth | 10 g. |
| 3,3-Dimethylglutaric acid | 3 g. |
| 5% Aqueous polyacrylamide solution | 20 g. |
| Dyphylline | 5 g. |
| Water | 10 g. |

The coating solution was coated on the absorbent layer to form a porous diazonium salt layer. After 30 min., a blushed polymer (Fuji Microfilter FM 300: trademark of Fuji Photo Film Co., Ltd., mean pore size 3.0 μm, thickness 180 μm) was pressed onto the diazonium salt layer and then dried to form a porous spreading layer. Thus, a multilayer analytical element was prepared.

On the analytical element was spotted 10 μl. of Versatol P (direct bilirubin content 3.8 mg/dl, total bilirubin content 18.6 mg/dl) or Omega (high bilirubin content) standard solution (direct bilirubin content 10.9 mg/dl, total bilirubin content 19.9 mg/dl). The analytical element was then incubated at 30° C. for 6 min. and formed color was measured by reflection photometry at 550 nm. The results are set forth in Table 4.

TABLE 4

| Diazonium Salt | Optical Density | |
|---|---|---|
| | Versatol P | Omega(high bilirubin content) |
| 2 | 0.46 | 0.47 |
| 3 | 0.49 | 0.50 |
| 5 | 0.48 | 0.49 |
| 6 | 0.51 | 0.52 |
| 13 | 0.45 | 0.46 |
| 16 | 0.47 | 0.47 |
| 17 | 0.45 | 0.46 |
| 18 | 0.50 | 0.51 |

Remark: The numbers given in Table 4 correspond respectively to the numbers described hereinbefore for listing the representative examples of the aryldiazonium salt according to the present invention. Accordingly, these numbers indicate the following compounds:

2: 2-methoxy-5-(tetradecyloxycarbonyl)benzenediazonium hexafluoroborate,
3: 2-ethoxy-5-(hexadecyloxycarbonyl)benzenediazonium tetrafluoroborate,
5: 2-methoxy-5-[β-(2',4'-di-t-amylphenoxy)ethoxycarbonyl]benzenediazonium tetrafluoroborate,
6: 2-methoxy-5-(N-hexadecylsulfamoylbenzenediazonium tetrafluoroborate,
13: 4-(hexadecyloxycarbonyl)benzenediazonium tetrafluoroborate,
16: 3-(N-tetradecylcarbamoyl)benzenediazonium tetrafluoroborate,
17: 2-methyl-5-tetradecyloxycarbonylbenzenediazonium tetrafluoroborate, and
18: 2-butyl-5-decyloxycarbonylbenzenediazonium tetrafluoroborate.

EXAMPLE 5

Preparation of Coating Solution for Formation of Porous Diazonium Salt Layer

In a mixture of 5 ml. of ethanol and 2 ml. of acetone was dissolved 37.5 mg. of 2-methoxy-5-(tetradecyloxycarbonyl)benzenediazonium tetrafluoroborate. The resulting solution was dispersed homogeneously in 10 g. of 5% aqueous solution of methyl vinyl ether - maleic anhydride (1:1, molar ratio) copolymer (inherent viscosity [$\eta$] in 1% methyl ethyl ketone solution at 25° C.: 2.6-3.5). To the resulting dispersion were added successively 30 ml. of water, 7.5 g. of microcrystalline cellulose (mean particle size 6 μm), and 8 g. of dyphylline. The mixture was processed in a ultrasonic dispersing apparatus to give a homogeneous dispersion.

Preparation of Coating Solution for Formation of pH adjusting Layer

In 30 g. of 10% aqueous deionized-gelatin solution was homogeneously dispersed 2.5 ml. of divinylbenzene-2-(dimethylamino)ethyl acrylate copolymer latex solution (15%) to prepare the coating solution.

Preparation of Analytical Element for Quantitative Analysis of Bilirubin

On a transparent polyethylene terephthalate support (thickness 180 μm) was coated the coating solution for formation of pH adjusting layer to form a pH adjusting layer of 15 μm thick (thickness upon dryness). On the dried pH adjusting layer was coated the coating solution for formation of porous diazonium salt layer to form a porous diazonium salt layer of 30 μm thick (thickness upon dryness). After approx. 1 min., onto the slightly hardened diazonium salt layer was pressed a cotton cloth under a laminating roller, and the cotton cloth was then dried. Thus, an analytical element for quantitative analysis of bilirubin was prepared.

Analysis of Bilirubin

On the analytical element was spotted 10 μl. of a commercially available control. The analytical element was then incubated at 30° C. for 6 min. and the formed color was measured by reflection photometry at 550 nm. The results are set forth in Table 5.

TABLE 5

| | Total Bilirubin Content (mg/dl) | Optical Density (at 550 nm) |
|---|---|---|
| Human albumin solution | 0 | 0.169 |
| Versatol | 1.10 | 0.207 |
| Q-PAK I | 1.26 | 0.215 |
| Calibrate I | 1.81 | 0.211 |
| Monitrol I | 1.81 | 0.224 |
| Calibrate II | 3.36 | 0.304 |
| Monitrol II | 4.24 | 0.321 |
| Q-PAK II | 4.77 | 0.341 |
| Calibrate III | 5.07 | 0.350 |
| Versatol P | 18.6 | 0.644 |
| Omega (high bilirubin content) | 19.8 | 0.675 |

Remark: The total bilirubin content of each cotrol was quantitatively measured in the manner as described in Example 1 using ABA-200 available from Abbott Laboratories.

What is claimed is:

1. An analytical element for the quantitative analysis of bilirubin in a liquid sample by a diazo method which comprises:
    a liquid impermeable, light-transmissive support;
    a porous reagent layer comprising a nondiffusive aryldiazonium salt, the aryl group of which having at least one substituent selected from the group consisting of an alkoxycarbonyl group, an alkylaminosulfonyl group and an alkylaminocarbonyl group, which is contained in a porous matrix comprising solid fine particles and an acidic polymer binder; and
    a liquid sample-spreading layer.

2. The analytical element as claimed in claim 1, in which said aryl group of the aryldiazonium salt further contains at least one substituent selected from the group consisting of an alkyl group and an alkoxy group.

3. The analytical element as claimed in claim 1 or 2 in which the acidic polymer comprises at least one repeating unit derived from styrene-p-sulfonic acid, acrylic acid, methacrylic acid, or a maleic acid derivative.

4. The analytical element as claimed in claim 3 in which the acidic polymer is a homopolymer having a repeating unit derived from styrene-p-sulfonic acid, acrylic acid, methacrylic acid, or a maleic acid derivative.

* * * * *